(12) United States Patent
Furuzono et al.

(10) Patent No.: US 7,473,731 B2
(45) Date of Patent: Jan. 6, 2009

(54) HYDROXYAPATITE COMPOSITE AND MANUFACTURING METHOD THEREOF, MEDICAL MATERIAL USING HYDROXYAPATITE COMPLEX

(75) Inventors: Tsutomu Furuzono, Suita (JP); Akio Kisida, Toyonaka (JP); Junzo Tanaka, Tsukuba (JP); Atsushi Matsuda, Tsukuba (JP)

(73) Assignees: Japan Science & Technology Agency, Saitama (JP); Japan As Represented By The President., Osaka (JP); Independent Administration Instit., Ibaraki (JP)

( * ) Notice: Subject to any disclaimer, the term of this patent is extended or adjusted under 35 U.S.C. 154(b) by 126 days.

(21) Appl. No.: 10/506,429

(22) PCT Filed: May 29, 2003

(86) PCT No.: PCT/JP03/06752

§ 371 (c)(1),
(2), (4) Date: Sep. 2, 2004

(87) PCT Pub. No.: WO03/102059

PCT Pub. Date: Dec. 11, 2003

(65) Prior Publication Data

US 2005/0119732 A1 Jun. 2, 2005

(30) Foreign Application Priority Data

| May 30, 2002 | (JP) | ............................. 2002-158278 |
| Apr. 25, 2003 | (JP) | ............................. 2003-122961 |

(51) Int. Cl.
C08L 83/02 (2006.01)
(52) U.S. Cl. .................. 524/588; 524/417; 524/871
(58) Field of Classification Search .................. 524/588, 524/417, 871
See application file for complete search history.

(56) References Cited

U.S. PATENT DOCUMENTS 4,276,135 A * 6/1981 Sato et al. ...................... 522/99
5,814,681 A * 9/1998 Hino et al. ................... 523/113

FOREIGN PATENT DOCUMENTS

| JP | 63-270061 | 11/1988 |
| JP | 07-303691 | 11/1995 |
| JP | 07-306201 | 11/1995 |
| JP | 08-056963 | 3/1996 |
| JP | 10-015061 | 1/1998 |
| JP | 2000-342676 | 12/2000 |
| JP | 2001-172511 | 6/2001 |
| JP | 2002-114859 | 4/2002 |

OTHER PUBLICATIONS

J. Materials Science: Materials in Medicine 15 (2004) 19-23 Furuzono et al Nano-scaled hydroxyapatite/polymer composite I. Coating of sintered hydroxyapatite particles on etc.
New Development trend of Intelligent material/technology Chapter 5: Percutaneous device Furuzono et al.
Extracted Article of Nanobio Engineering Materials March issue 2004 Chapter 8 Characteristis of Single crystal apatite/Polymr composite surface Furuzono et al.
Nikkei Advanced Technology Report 43 Aug. 11 issue, 2003.
Forefront of JST Fundamental Research No. 4 Jan. 2004 Japan Science and Technology Agency.
Proceedings of Annual Meeting of The Society of Polymer Science, Japan 2003, vol. 52(7), No. 5 (2003).
Proceedings of 41st meeting of Japanese Society for Artificial Organs IIIPb186, Polymer Preprints, Japan vol. 53(1) (2004) p. 2149.
Polymer Preprints, Japan vol. 52, No. 1. (2003).
The 24th Annual Meeting of the Japanese Society for Biomaterials, Nov. 19, 2002.
The First International Congress on Bio-Nanointerface, May 19-24, 2003,Tokyo Japan.
The Japanese Journal of Artificial Organs, vol. 32, No. 2, Published Sep. 15, 2003.
New Development Trend of Intelligent Material/Technology-Chapter 5: Percutaneous device, Furuzono et al. (Published: Apr. 30, 2003).
Development of Bio-interface Consisting of Nano-Scaled Hydroxyapatite and Polymer Fibers via Covalent Linkage for Implant Materials, p. 130, Furuzono et al, The First International Congress on Bio-Nanointerface, ICBN 2003 Tokyo (May 19-24, 2003).

* cited by examiner

*Primary Examiner*—Kuo-Liang Peng
(74) *Attorney, Agent, or Firm*—Nixon & Vanderhye PC (57) ABSTRACT

A hydroxyapatite complex includes a hydroxyapatite sintered compact that is chemically bonded to a polymer-based material containing at least one functional group selected form a group consisting of an isocyanate group and an alkoxysilyl group, wherein: the hydroxyapatite sintered compact is reacted with the functional group of the polymer-based material. This arrangement allows manufacturing of a hydroxyapatite complex without a chemical pre-treatment of the hydroxyapatite sintered compact.

9 Claims, 5 Drawing Sheets

HYDROXYAPATITE COMPOSITE AND MANUFACTURING METHOD THEREOF, MEDICAL MATERIAL USING HYDROXYAPATITE COMPLEX

This application is the US national phase of international application PCT/JPO3/06752 filed 29 May 2003, which designated the US and claims priority to IP Application No. 2002-158278 filed 30 May 2002 and JP Application No. 2003-122961 filed 25 April 2003. The entire contents of these applications are incorporated herein by reference.

TECHNICAL FIELD

The present invention relates to a hydroxyapatite complex and a manufacturing method thereof. The hydroxyapatite complex has biocompatibility, and an adhesion property (adhesiveness) with respect to a living organism, and is suitably used for medical purposes. The present invention further relates to a medical material using the hydroxyapatite complex.

BACKGROUND ART

A polymer-based material, for example, a silicone rubber or polyurethane, is widely used as a medical material such as a percutance trans-catheter, because of its bioinertness, long-term stability, strength, flexibility etc. However, since the polymer-based material with bioinertness does not adhere to the dermal living organism, it commonly causes a risk of Down-growth (a phenomenon in which epithelial tissue invaginate into the skin along the surface of the catheter), and a risk of bacterial infection of the invaginate portion.

Meanwhile, calcium phosphate, for example, a hydroxyapatite, is also widely used as a bioactive material in the medical field as such, or as a complex with an inorganic material or an organic material. Percutaneous trans-catheter is one of applications of such a calcium phosphate. However, the calcium phosphate is fragile, poor in formability, and has no affinity to a metal material. Therefore, when the calcium phosphate is used for a percutaneous trans-catheter, it may cause bacterial infection via the gap between the metal material and the calcium phosphate terminal.

In view of this problem, a hydroxyapatite complex has been suggested. The hydroxyapatite complex is made of a polymer-based material whose surface is modified by calcium phosphate such as hydroxyapatite.

To modify the surface of a polymer-based material by calcium phosphate, some different methods have been disclosed, for example, a modification method using sputtering ion beam (Document 1: Japanese Laid-Open Patent Application Tokukaihei 08-56963/1996, published on Mar. 5, 1996), a modification method using plasma treatment (Document 2: Japanese Laid-Open Patent Application Tokukaihei 07-303691/1996, published on Nov. 21, 1995), a modification method by complexation with glass (Document 3: Japanese Laid-Open Patent Application Tokukaisho 63-270061/1988, published on Nov. 8, 1988), a modification method using vital imitation reaction (Document 4: Japanese Laid-Open Patent Application Tokukaisho 07-306201/1995, published on Nov. 21, 1995), and a modification method using alternate immersion (Document 5: Japanese Laid-Open Patent Application Tokukai 2000-342676/2000, published on Dec. 12, 2000).

However, since the calcium phosphate used in the modification methods of the foregoing publications has an amorphous structure, it is easily dissolved in a living body. Therefore, this calcium phosphate is not desirable in terms of persistence of bioactivity. Accordingly, the calcium phosphate is suitable for a usage in which the calcium phosphate is dissolved in a living body (for example, a bone-substitution material), but not suitable for a usage in which the calcium phosphate is kept in the body for a long-period (for example, percutance terminal). Further, in the modification methods disclosed in the foregoing publications, the calcium phosphate is physically or electrostatically fixed into the base-material, which does not ensure sufficient strength in adherence.

In this view, there has been a demand for alternative method for modifying the surface of the polymer-based material by the calcium phosphate for the usage where the calcium phosphate is kept in a body for a long-period. An alternative to solve this problem can be found in Document 6 (Japanese Laid-Open Patent Application Tokukaihei 10-15061/1998, published on Jan. 20, 1998) or Document 7 (Japanese Laid-Open Patent Application Tokukai 2001-172511/2001, published on Jun. 26, 2001).

The Document 6 discloses an intraperitoneal indwelling catheter, which is created by fixing ceramic porous particles to the surface of the polymer-based material by an adhesive, or by fusing the polymer-based material so that the ceramic porous particles are fixed on the surface.

However, in the method of Document 6, the ceramic porous particles are physically fixed into the base-material, and therefore it cannot ensure strength in adherence.

Further, in the method of fixing the ceramic porous particles into the surface of the polymer-based material by an adhesive, the ceramic porous particles may be laminated on the surface of the polymer-based material. This may cause ruin of physicality of the polymer-based material, or elution of the adhesive.

Further, in the method of fusing the polymer-based material so that the ceramic porous particles are fixed to the surface, body fat may permeate into the polymer-based material via the fixing portion, which can ruin physicality of the polymer-based material.

Further, the method of Document 7 requires a chemical pre-treatment to introduce an active group into the calcium phosphate.

In the presence of such problems, there is a demand for an alternative method for modifying the polymer-based material by the calcium phosphate which enables the calcium phosphate to be easily fixed to the surface of the polymer-based material for a long period without loosing bioactivity, as well as a demand for a calcium phosphate complex (hydroxyapatite complex) obtained by the method.

DISCLOSURE OF INVENTION

In order to solve the foregoing problems, the inventors of the present invention had intensive studies with regard to a hydroxyapatite complex and manufacturing method thereof. Then the inventors have succeeded to solve the problems with the use of a specific compound of calcium phosphate, and also a specific functional group to be introduced in the polymer-based material.

Specifically, in order to solve the foregoing problems, the present invention provides a manufacturing method of a hydroxyapatite complex including a hydroxyapatite sintered compact and a polymer-based material, comprising the step of: a) reacting the hydroxyapatite sintered compact with a functional group of the polymer-based material, that contains at least one functional group selected from a group consisting of an isocyanate group and an alkoxysilyl group, so as to chemically bond the hydroxyapatite sintered compact and the polymer-based material.

The hydroxyapatite sintered compact is obtained through sintering of hydroxyapatite. More specifically, the hydroxyapatite sintered compact may be obtained by sintering hydroxyapatite for a predetermined time at a temperature ranging form 800° C. to 1300° C. The particles of the hydroxyapatite sintered compact contain $Ca_{10}(PO_4)_6(OH)_2$ on the surfaces. Further, the hydroxyapatite sintered compact may contain a compound in which the hydroxide ion and/or phosphate ion of the hydroxyapatite is partly replaced to carbonate ion, chloride ion, fluoride ion or the like, or may contain tricalcium phosphate etc.

Further, the polymer-based material contains at least one functional group selected from a group consisting of an isocyanate group and an alkoxysilyl group.

With this structure, the hydroxyapatite sintered compact is reacted with the functional group of the polymer-based material. The isocyanate group and/or the alkoxysilyl group is chemically bonded directly with a hydroxyl group (—OH) contained in the hydroxyapatite sintered compact.

On this account, in contrast to the conventional method, it is not necessary to introduce an active group in the hydroxyapatite sintered compact in order to react the functional group with the active group. Namely, it is not necessary to perform a chemical pre-treatment with respect to the hydroxyapatite sintered compact, thus performing manufacturing of the hydroxyapatite complex in an easier way than the conventional way.

Further, since this method allows omission of the chemical pre-treatment, there are no risks of degradation or changes in bioactivity of the hydroxyapatite sintered compact.

Further, in order to solve the foregoing problems, the present invention provides a manufacturing method of a hydroxyapatite complex including a hydroxyapatite sintered compact and a polymer-based material, comprising the steps of: a) introducing at least one functional group selected from a group consisting of an isocyanate group and an alkoxysilyl group into the polymer-based material; and b) reacting the hydroxyapatite sintered compact with the functional group of the polymer-based material so as to chemically bond the hydroxyapatite sintered compact with the polymer-based material.

The foregoing structure uses a polymer-based material in which at least one functional group selected from a group consisting of an isocyanate group and an alkoxysilyl group is introduced. This structure allows the use of various polymer-based materials.

With the foregoing structure, the hydroxyapatite sintered compact is chemically bonded directly with the isocyanate group and/or the alkoxysilyl group. Therefore, in contrast to the conventional method, it is not necessary to introduce a reactive functional group in the hydroxyapatite sintered compact in order to react the functional group with the reactive functional group. Namely, it is not necessary to perform a chemical pre-treatment with respect to the hydroxyapatite sintered compact, thus performing manufacturing of the hydroxyapatite complex in an easier way. Further, in order to solve the foregoing problems, the present invention provides a hydroxyapatite complex in which a hydroxyapatite sintered compact and a polymer-based material containing an isocyanate group and/or an alkoxysilyl group are chemically bonded, wherein: the hydroxyapatite sintered compact is chemically bonded directly to the isocyanate group and/or the alkoxysilyl group of the polymer-based material.

In the foregoing structure in which the hydroxyapatite sintered compact is chemically bonded directly to the isocyanate group and/or the alkoxysilyl group of the polymer-based material, the isocyanate group and/or the alkoxysilyl group is actually chemically bonded to the hydroxyl group (—OH) contained in the hydroxyapatite sintered compact.

With the foregoing structure in which the hydroxyapatite sintered compact is chemically bonded directly to the isocyanate group and/or the alkoxysilyl group of the polymer-based material, it is not necessary to perform a chemical pre-treatment with respect to the hydroxyapatite sintered compact, in contrast to the conventional method.

Further, in the foregoing structure, the hydroxyapatite sintered compact is chemically bonded directly to the functional group (the isocyanate group and/or the alkoxysilyl group) of the polymer-based material. Therefore, the structure is immune to the problem of residue of the active group on the surface of the calcium phosphate in contrast to the conventional method in which an active group is introduced in calcium phosphate. Thus, in contrast to the conventional structure, this structure is immune to a risk of degradation in bioactivity of the calcium phosphate due to the residue of the active group.

Further, in order to solve the foregoing problems, the present invention provides a hydroxyapatite complex in which a hydroxyapatite sintered compact and a polymer-based material containing an alkoxysilyl group are chemically bonded, wherein: the hydroxyapatite sintered compact is chemically bonded to the polymer-based material with a molecular chain expressed as:

(1)

where X expresses the polymer-based material, and Y expresses the hydroxyapatite sintered compact.

Further, in order to solve the foregoing problems, the present invention provides a medical material using the hydroxyapatite complex.

With the use of the foregoing hydroxyapatite complex, it is possible to provide a medical material with high bioactivity and improved reliability.

For a fuller understanding of the nature and advantages of the invention, reference should be made to the ensuing detailed description taken in conjunction with the accompanying drawings.

BEST MODE FOR CARRYING OUT THE INVENTION

One embodiment of the present invention is described below.

A hydroxyapatite complex according to the present embodiment is manufactured by chemically bonding a hydroxyapatite sintered compact and a polymer-based material containing an isocyanate group and/or an alkoxysilyl group. The hydroxyapatite complex has a structure in which a hydroxyl group (—OH) contained in the hydroxyapatite sintered compact and the isocyanate (—NCO) group or the alkoxysilyl (≡Si (OR)) group contained in the polymer-based material are directly bonded in a chemical manner. In the present embodiment, the alkoxysilyl group refers to a group including Si—OR. More specifically, the alkoxysilyl group contains —Si—OR, =Si—(OR)2, —Si—(OR)3 etc. Note that, The signs = and ≡ in the formulas do not necessarily represent a double bond and a triple bond. The Si may be bonded to either a single base or differing bases through the bond(s). Accordingly, the alkoxysilyl group also includes —SiH—(OR)2 or —SiH2—(OR) etc. Further the "R" in the formula Si—OR refers to an alkyl group or hydrogen.

[Hydroxyapatite Sintered Compact]

The hydroxyapatite sintered compact (also referred to as a hydroxyapatite ceramics) according to the present embodiment is created by sintering an amorphous hydroxyapatite, a kind of calcium phosphate. More specifically, a hydroxyapatite sintered compact may be obtained, for example, by sintering an amorphous hydroxyapatite at a temperature range between 800° C. and 1300° C. for a predetermined time. Through the sintering, crystallization of the hydroxyapatite increases, and therefore, for example, solubility thereof may be reduced when introduced into a living body. The degree of crystallization of the hydroxyapatite sintered compact may be measured by an X-ray diffraction (XRD) method, for example. Concretely, the crystallization increases as the half bandwidth of the peak of the crystallization surface becomes narrower.

Further, the hydroxyapatite sintered compact of the present embodiment contains $Ca_{10}(PO_4)_6(OH)_2$ on its surface. The hydroxyapatite sintered compact requires the presence of $Ca_{10}(PO_4)_6(OH)_2$ on its surface in an amount of approximately 0.1% by weight with respect to the whole amount of the hydroxyapatite sintered compact. However, the hydroxyapatite sintered compact preferably contains $Ca_{10}(PO_4)_6(OH)_2$ of equal to or greater than 50% by weight, and further preferably, equal to or greater than 90% by weight. This $Ca_{10}(PO_4)_6(OH)_2$ on the surface allows the hydroxyapatite sintered compact to be directly bonded with a functional group of a polymer-based material (described later). Further, the hydroxyapatite sintered compact may contain a compound created by partly substituting hydroxide ion and/or phosphate ion of hydroxyapatite by carbonate ion, chloride ion, fluoride ion etc. Further, the hydroxyapatite sintered compact may contain tricalcium phosphate which is generated upon sintering of an amorphous hydroxyapatite.

With its superior affinity to a living organism and superior stability in a living body environment, the hydroxyapatite sintered compact of the present embodiment is suitable for a medical material. Further, the hydroxyapatite sintered compact of the present embodiment is not likely to be dissolved in a living body. On this account, the hydroxyapatite sintered compact of the present embodiment maintains its bioactivity in a living body for a long period.

Here, a manufacturing method of the hydroxyapatite sintered compact is explained below. The hydroxyapatite sintered compact of the present embodiment may be obtained by sintering an amorphous hydroxyapatite. The hydroxyapatite may be artificially manufactured through a publicly-known method such as a wet way, a dry way, a hydrolysis method, or a hydrothermal method. Otherwise, the hydroxyapatite may be derived from a natural bone, a tooth, etc.

The hydroxyapatite is preferably sintered at equal to or grater than 800° C. at lowest. More preferably, the sintering is performed at not less than 900° C., and further preferably at not less than 1000° C. Carrying out sintering at lower than 800° C. may result in insufficient sintering. As to the upper limit of the temperature for sintering, it preferably is not higher than 1300° C., more preferably not higher than 1250° C., and further preferably not higher than 1200° C. If the sintering temperature exceeds 1300° C., the hydroxyapatite may be resolved or the number of hydroxyl groups in the sintered compact may decrease as the ratio of tricalcium phosphate increases. As a result, there arise some difficulties for direct bond of the hydroxyapatite sintered compact with the functional group of the polymer-based material. Thus, the sintering temperature should be set within the foregoing range for creating a hydroxyapatite sintered compact which can be directly bonded with a functional group of a polymer-based material, and is not easily dissolved in a living body (high in crystallization). The sintering time is not limited but may be appropriately decided in each case.

It is preferable that the hydroxyapatite sintered compact is in the form of particles. The particles may have any shape and diameter allowing themselves to be fixed into the surface of the polymer-based material when the hydroxyapatite sintered compact is chemically bonded with a polymer-based material (described later). Specifically, the lower limit of the diameter is preferably not less than 0.001 µm, more preferably not less than 0.01 µm. In the form of particles with diameters less than 0.001 µm, the hydroxyapatite sintered compact fixed into the surface of the polymer-based material (described later) will be dissolved when a hydroxyapatite complex is implanted in a loving body, thereby causing a risk of deterioration of biocompatibility. The upper limit of the diameter is preferably not more than 1000 µm, and more preferably not more than 100 µm. If the particles have diameters greater than 1000 µm, the bond of the hydroxyapatite sintered compact with a polymer-based material (described later) becomes relatively weak, and may cause breakage of a resulting hydroxyapatite complex when the complex is implanted in a living body.

Further, the sintering temperature and the diameter of the hydroxyapatite sintered compact may be controlled, for example, in order to control dissolving speed of the hydroxyapatite sintered compact when the resulting hydroxyapatite complex is implanted in a living body. Namely, the specified temperature and diameter enable designing in physicality of a hydroxyapatite complex according to the usage.

[Polymer-Based Material]

The polymer-based material according to the present embodiment is preferable made of a medical polymeric material, more preferably an organic polymeric material. Specifically, the polymer-based material may be made of a synthetic polymer, such as a silicone polymer (or silicone rubber), polyethylene glycols, polyalkylene glycols, polyglycol acid, polylactic acid, polyamide, polyurethane, polysulfone, polyether, polyether ether ketone, polyamine, polyurea, polyimide, polyester, polyethylene, polypropylene, polytetrafluoroethylene, polyacrylic acid, polymethacrylic acid, polymethyl methacrylate, polyacrylonitrile, polystyrene, polyvinyl alcohol, or polyvinylchloride; or a natural polymer, such as a polysaccharide, such as cellulose, amylase, amylopectin, chitin, or chitosan, polypeptide such as collagen, mucopolysaccharide such as hyaluronic acid, chondroitin, chondroitin sulfate, or silk fibroin etc. Among these, silicone polymer, polyurethane, polytetrafluoroethylene, or silk fibroin is preferably used in terms of stability in a long-term, and of superiority in strength and flexibility etc.

Further, instead of the foregoing polymer-based materials, an inorganic base material, such as titanium oxide etc. is suitable for a medical material. Accordingly, the polymer-based material of the present invention also includes an inorganic material such as the titanium oxide.

The polymer-based material of the present embodiment includes at least one functional group selected from a group of isocyanate group or alkoxysilyl group. The functional group exists on the surface of the polymer-based material. The functional group on the surface of the polymer-based material may be contained in the polymer on the surface of the base material, or may be introduced by modifying the polymer-based material through a publicly-known method such as an acid/alkali treatment, corona discharge, plasma irradiation, or surface graft polymerization.

Further, to introduce the functional group, an active group may be introduced into the polymer-based material so as to enable introduction of the functional group. The method for introducing the functional group into the polymer-based material will be described later.

Further, the polymer-based material can be in the form of a sheet, a fiber, a tube or a madreporite. An appropriate form may be selected according to the usage.

[Manufacturing Method of a Hydroxyapatite Complex]

A manufacturing method of a hydroxyapatite complex according to the present embodiment is described below.

A manufacturing method of a hydroxyapatite complex according to the present embodiment carries out a process for reacting at least one functional group contained in the polymer-based material with respect to a hydroxyapatite sintered compact (To be more specific, a hydroxyl group contained in the hydroxyapatite sintered compact). The functional group is selected from an isocyanate group and an alkoxysilyl group.

Further, in the case where the polymer-based material does not contain the at least one functional group of either an isocyanate group or an alkoxysilyl group, an introduction process is required before the reaction process so as to introduce the at least one functional group of either an isocyanate group or an alkoxysilyl group into the polymer-based material. The hydroxyapatite complex of the present embodiment may be obtained through these two processes.

[Introduction Process]

In the introduction process, a functional group (an isocyanate group and/or an alkoxysilyl group) is introduced into the polymer-based material (the surface of a polymer-based material). Note that, the following describes the case where an alkoxysilyl group is introduced into the polymer-based material.

There is no restriction for the method for introducing a functional group into the polymer-based material, i.e., the introduction process, and it may be carried out by a publicly-known method. However, by treating the end of molecule with a silane coupling agent etc. having a reactive functional group, the functional group may be introduced into the polymer-based material.

Here, an example of the introduction method of an alkoxysilyl group into the polymer-based material is explained below. This method uses a silane coupling agent. Note that, the method for introducing an alkoxysilyl group into the polymer-based material is not limited the method below, but may be performed by various manners.

The silane coupling agent has a chemical structure as given by the following chemical formula (2).

Z-Si≡(OR)3 (2)

The Z may be any reactive functional group which causes chemical bond with an organic material (a polymer-based material) such as various synthetic resins. Specifically, it may be a vinyl group, an epoxy group, an amino group, (meta) acryloxy group, mercapto group etc. Further, the OR may be any material that causes chemical bond with an inorganic material (hydroxyapatite sintered compact). Specifically, it may be a methoxy group, ethoxy group etc. Further, in the chemical formula (2), the Z and Si, the reactive functional groups, may be bonded by a polymer chain, a low molecular chain, or may otherwise be directly bonded.

A specific example of the silane coupling agent may be a vinyl silane coupling agent, such as vinyltrichlorosilane, vinyltrimethoxysilane, vinyltriethoxysilane; an epoxy silane coupling agent such as β-(3,4epoxycyclohexyl) ethyltrimethoxysilane, γ-glycidoxypropyltrimethoxysilane, γ-glycidoxypropylmethyldiethoxysilane, γ-glycidoxypropyltriethoxysilane; a styryl silane coupling agent, such as p-styryltrimethoxysilane; a methacryloxy silane coupling agent, such as γ-methacryloxypropylmethyldimethoxysilane, γ-methacryloxypropyltrimethoxysilane, γ-methacryloxypropylmethyldiethoxysilane, γ-methacryloxypropyltriethoxysilane; an acryloxy silane coupling agent, such as γ-acryloxypropyltrimethoxysilane; an amino silane coupling agent, such as N-β(aminoethyl) γ-aminopropyltrimethoxysilane, N-β(aminoethyl) γ-aminopropylmethyldimethoxysilane, N-β(aminoethyl) γ-aminopropyltriethoxysilane, γ-aminopropyltrimethoxysilane, γ-aminopropyltriethoxysilane, γ-triethoxy-N-(1,3-dimethylbutylidene) propylamine, N-phenyl-γ-aminopropyltrimethoxysilane, hydrochloride of N-(vinylbenzil)-β-aminoethyl-γ-aminopropyltrimethoxysilane, special aminosilane; an ureide silane coupling agent, such as γ-ureidopropyltriethoxysilane; a chloropropylsilane coupling agent, such as γ-chloropropyltrimethoxysilane; an mercapto silane coupling agent, such as γ-mercaptopropyltrimethoxysilane, γ-mercaptopropylmethyldimethoxysilane; a sulfidesilane coupling agent, such as bis (triethoxypropyl) tetrasulfide; an isocyanate silane coupling agent, such as γ-isocyanatepropyltriethoxysilane. Among these, the γ-methacryloxypropyltrimethoxysilane, a polymeric monomer, is particularly suitable. However, an appropriate silane coupling agent may be selected according to, for example, the type of polymer-based material, or the type of active group (described later) in the case where an active group is introduced in the surface of the polymer-based material.

The method for introducing an alkoxysilyl group into the polymer-based material using the silane coupling agent listed above may be carried out by directly introducing a silane coupling agent, that contains a reactive functional group in its molecular end, into a polymer-based material having been through a corona treatment, for example. Alternately, the polymer-based material may be directly bonded with a non-aqueous monomer containing the functional group through graft polymerization, by taking out a proton (hydrogen atom) from the polymer-based material by a surfactant and a peroxide initiator so that the polymer-based material becomes in radical state. This method enables direct introduction of the functional group into the polymer-based material.

Furthermore, the introduction method may also be performed by previously introducing an active group into the polymer-based material so that the active group is reacted with the reactive functional group contained in the silane coupling agent. Specific examples of the active group may be a vinyl group, an amino group, etc. However, the active group is not limited to these groups, but may be selected according to the type of the reactive functional group (the Z in the chemical formula (2)) of the silane coupling agent.

As an example of the foregoing method, the following describes concrete condition of a method for introducing an alkoxysilyl group into the polymer-based material by previously introducing a vinyl group as an active group into a silk fibroin as the polymer-based material, so as to react the vinyl group with the reactive functional group of the silane coupling agent.

First explained is a process (active group introduction process) for introducing an active group into the polymer-based material. To introduce a vinyl group into the polymer-based material, the polymer-based material is reacted with a compound containing an active group, in a mixed solution made of a catalyst, a polymerization inhibitor, and a solvent.

Specific examples of this compound containing the active group may be 2-methacryloyloxyethylisocyanate, hexamethylenediisocyanate, etc. A polar solvent is preferably used as the solvent for the mixed solution, for example, such as anhydrous dimethylsulfoxide, anhydrous dimethylformamide etc. The polymerization inhibitor added to the mixed solution serves to prevent the active groups introduced in the polymer-based material from polymerizing to each other and also prevents compounds containing the active groups from polymerizing to each other. The polymerization inhibitor may be hydroquinone, for example. The catalyst may be dibutyltin (IV) dilaurate, for example.

As to the addition amount of the compound containing the active group, the upper limit is preferably not less than 10% by weight, more preferably not less than 50% by weight, and further preferably not less than 100% by weight with respect to the polymer-based material. If the addition amount is less than 10% by weight, the polymer-based material after the introduction process may not have sufficient amount of the active group. As to the upper limit, it is preferably not more than 500% by weight, more preferably not more than 400% by weight, and further preferably not more than 300% by weight. The ratio more than 500% by weight is not preferable in the economic view.

As to the lower limit of the reaction temperature, it is preferably not less than 30° C., more preferably not less than 40° C., and further preferably not less than 45° C. The reaction temperature less than 30° C. may cause inadequate reaction, and may also cause failure of introduction of the active group into the polymer-based material. As to the upper limit of temperature, it is preferably not more than 100° C., more preferably not more than 80° C., and further preferably not more than 60° C. The reaction temperature more than 100° C. may cause the active groups to react to each other, or may cause degradation of the polymer-based material. The reaction time may be decided according to the reaction temperature and/or other factors. By carrying out the reaction process under such a condition, an active group may be easily introduced into a polymer-based material.

As to the lower limit of the introduction ratio (% by weight), it is preferably not less than 0.1% by weight, more preferably not less than 1.0% by weight, and further preferably not less than 2.0% by weight. With the introduction ratio less than 0.1% by weight, the number of alkoxysilyl groups introduced into the polymer-based material decreases, and may result in failure of manufacturing of a hydroxyapatite complex. As to the upper limit of the introduction ratio with respect to the polymer-based material, it is preferably not more than 30% by weight, more preferably not more than 25% by weight, and further preferably not more than 20% by weight. With the introduction ratio more than 30% by weight, the number of alkoxysilyl groups introduced into the polymer-based material increases, and may cause the respective active groups to react to each other.

Next, the active groups of the polymer-based material are polymerized to the silane coupling agent containing reactive functional groups in its end, so as to introduce the alkoxysilyl groups in the polymer-based material.

There is no limitation in selecting the silane coupling agent, and it may be any kinds containing reactive functional groups in its end that enables polymerization with the active groups introduced in the polymer-based material. However, in the case of using a vinyl group as the active group, a methacryloxy coupling agent, such as γ-methacryloxypropyltrimethoxysilane etc. may be preferably used.

Further, after introduction of the silane coupling agent and the active groups into the polymer-based material, the polymer-based material is subjected to polymerization in the presence of a polymerization initiator and a solvent so that an alkoxysilyl group is introduced in the polymer-based material.

A preferable example of the solvent may be a nonpolar organic solvent such as a hydrocarbon solvent, for example, toluene, hexan etc.

The polymerization initiator may be azobisisobutyronitrile, benzoyl peroxide etc.

As to the lower limit of the usage amount (addition amount) of the silane coupling agent, it is preferably not less than 10% by weight, more preferably not less than 50% by weight, and further preferably not less than 100% by weight with respect to the polymer-based material in which the active group is introduced. If the amount of the silane coupling agent is less than 10% by weight, it may cause insufficient introduction of alkoxysilyl groups into the polymer-based material, and may further cause failure of reaction to a desired amount of hydroxyapatite sintered compact. As to the upper limit of the usage amount, it is preferably not more than 500% by weight, more preferably not more than 400% by weight, and further preferably not more than 300% by weight. The usage amount more than 500% by weight is not preferable in the economic view.

Further, it is more preferable that the polymerization is performed in a nitrogen atmosphere. As to the lower limit of the polymerization temperature, it is preferably not less than 40° C., more preferably not less than 45° C., and further preferably not less than 50° C. The reaction temperature less than 40° C. may cause inadequate polymerization, and may also cause failure of introduction of the functional group into the polymer-based material. As to the upper limit of the polymerization temperature, it is preferably not more than 80° C., more preferably not more than 75° C., and further preferably not more than 70° C. The polymerization temperature more than 80° C. may cause degradation of the polymer-based material. For the time for polymerization, an appropriate time may be decided in view of the desired introduction ratio (the rate of introduction of the functional group into the polymer-based material).

Further, as to the lower limit of the introduction ratio (% by weight) of the functional group into the polymer-based material, it is preferably not less than 0.1% by weight, more preferably not less than 1% by weight. The introduction ratio here refers to an amount (weight) of the silane coupling agent introduced into the polymer-based material, with respect to per weight unit of the polymer-based material. If the introduction ratio is equal to or more than 0.1% by weight, sufficient amount of a hydroxyapatite sintered compact may be bonded with the polymer-based material so that the polymer-based material expresses a desirable biocompatibility. The upper limit of the introduction ratio is not particularly limited. However, when the introduction ratio exceeds 100% by weight, the amount of the hydroxyapatite sintered compact to be bonded to the polymer-based material may become more than required. This is not preferable in the economic view.

Note that, the introduction of an alkoxysilyl group into the polymer-based material is not limited to the method above, but may be performed by various manners. Also, the reaction condition is not particularly limited, but may be determined according to the type of the polymer-based material, the compound containing the active group, or the silane coupling agent etc. and/or other factors. With the described procedure, a functional group is introduced into the surface of the polymer-based material.

Here, the following describes another method of introducing the alkoxysilyl group into the polymer-based material. More specifically, this method is performed by reacting a silane coupling agent containing an alkoxysilyl group with the polymer-based material, so as to directly introduce the alkoxysilyl group into the polymer-based material.

Firstly, the silane coupling agent is mixed with a surfactant. Then, the resulting mixed agent is added into an aqueous solution containing a polymer-based material and an initiator so that the agent and the solution are reacted to each other. As a result, the alkoxysilyl group is directly introduced into the polymer-based material. In this introduction method, the reaction process is performed in the aqueous solution. On this account, the resulting polymer-based material in which the alkoxysilyl group is introduced ensures superior safety with respect to a living body.

The surfactant used for the direct introduction method of the alkoxysilyl group into the polymer-based material may be, for example, a nonionic surfactant, such as penta ethylene glycol dodecyl ether, hexaethylene glycol monododecyl ether, nonyl phenyl polyoxyethylene, polyoxyethylene (10) octyl phenyl ether, dodecyl-β-glycoside etc. Further, the initiator may be, for example, ammonium persulfate, potassium persulfate (potassium peroxydisulfate) etc. Further, a preferable example of the reaction solvent may be water, alcohol etc.

Further, in the direct introduction method of the alkoxysilyl group into the polymer-based material, the amount of the surfactant is preferably in a range from 1.0% to 50.0% by weight, and more preferably in a range from 10.0% to 25.0% by weight. With a surfactant in an amount in this range, the alkoxysilyl group contained in the silane coupling agent may be protected from the water or alcohol.

In other words, in the direct introduction method of the alkoxysilyl group into the polymer-based material, the alkoxysilyl group contained in the silane coupling agent, which includes the reactive functional group and the alkoxysilyl-group, is temporarily protected by a surfactant, and then, the reactive functional group in the silane coupling agent in which the protected alkoxysilyl group is protected is reacted to the polymer-based material, thereby directly introducing the alkoxysilyl group into the polymer-based material.

Note that, the other reaction conditions (e.g., the amount of the alkoxysilyl group added to the polymer-based material) etc. in the direct introduction method of the alkoxysilyl group into the polymer-based material are similar to those in the method above using an alkoxysilyl group as a functional group. Therefore, the minute explanation thereof is omitted here.

Next, the following describes the case where the functional group is an isocyanate group. In the case of carrying out polymerization of the polymer-based material and a monomer containing an isocyanate group in its end, in order to introduce the isocyanate group into the polymer-based material, there may be a problem of deactivation of the isocyanate group as a result of its reaction to active hydrogen in the reaction solvent. In this view, the reaction process is preferably carried out in an anhydrous solvent, such as anhydrous dimethyl sulfoxide, anhydrous dimethyl formamide etc.

Further, in the case of reacting the polymer-based material to a monomer containing an isocyanate group in its end in water or alcohol containing active hydrogen, the isocyanate group requires some protection not to react to the active hydrogen. More specifically, the polymerization process may be carried out by protecting the isocyanate group by a blocking agent, such as phenol, imidazole, oxime, N-hydroxyimide, alcohol, lactam, active methylene complex etc. This blocking agent for protecting the isocyanate group is detached by heat. Therefore, by heating the monomer containing the isocyanate group after it is subjected to polymerization to the polymer-based material with protection by a blocking agent, the isocyanate group may be introduced into the polymer-based material.

In the case of using phenol as the blocking agent, heating at 110° C. to 120° C. causes detachment of the blocking agent protecting the isocyanate group. Further, in the case of using imidazole as the blocking agent, heating at 110° C. to 130° C. causes detachment. Further, in the case of using oxime as the blocking agent, heating at 130° C. to 150° C. causes detachment. The blocking agent may be a phenol contained compound, such as methylsalicylate, methyl-p-hydroxybenzoate; imidazole; or a compound containing oxime, such as methylethylketoxime, acetoneoxime etc. Further, depending on the type of the polymer-based material, a compound containing N-hydroxyimide, such as N-hydroxy phthalimide, N-hydroxy succinimide; a compound containing alcohol, such as methoxy propanol, ethyl hexanol, pentol, ethyllactate; a compound containing lactam, such as caprolactam, pyrrolidinone; or an active methylene compound, such as ethyl acetoacetate etc. may also be used.

Note that, the other reaction conditions (e.g., the amount of the isocyanate group added to the polymer-based material) etc. in the foregoing introduction method of the isocyanate group as a functional group into the polymer-based material are similar to those in the method above of directly introducing an alkoxysilyl group into a polymer-based material. Therefore, the minute explanation thereof is omitted here.

[Reaction Process]

The reaction process is performed by reacting a hydroxyapatite sintered compact with the functional group (an isocyanate group and/or an alkoxysilyl group) in which the polymer-based material is introduced through the introduction process so as to cause chemical bond between those. More specifically, the polymer-based material is soaked by a dispersion liquid in which a hydroxyapatite sintered compact is dispersed so that the hydroxyapatite sintered compact is adhered to the surface of the polymer-based material. Then, a hydroxyl group of the hydroxyapatite sintered compact adhered to the surface is reacted to the functional group of the polymer-based material. The following describes a case where the polymer-based material is a silk fibroin, and the functional group is an alkoxysilyl group.

The dispersion medium for dispersing the hydroxyapatite sintered compact may be an organic solvent, for example, such as water; a hydrocarbon solvent, such as toluene, hexan, etc.; an alcohol; an ether solvent, such as tetrahydrofuran, diethylether etc.; a ketone solvent, such as acetone, methylethylketone etc. Among these, an alcohol is most preferably used, as it ensures superior dispersion of the hydroxyapatite sintered compact. Further, in the case of using a hydrocarbon solvent, such as toluene, hexan, etc., the following methods are suggested to ensure desirable dispersion of the hydroxyapatite sintered compact.

1) A method of powerfully stirring the solvent by a stirring device such as a stirring device
2) A method of dispersing the hydroxyapatite sintered compact by an ultrasonic device
3) A method of using both the stirrer and the ultrasonic device In preparing the dispersion liquid, the lower limit of the addition amount of the hydroxyapatite sintered compact is preferably not less than 0.01% by weight with respect to the dispersion medium, more preferably not less than 0.02% by weight, and further preferably not less than 0.05% by weight. If the addition amount of the hydroxyapatite sintered compact is less than 0.01% by weight, the hydroxyapatite sintered compact will not be evenly adhered to the surface of the polymer-based material, and therefore the coated surface may become uneven. As to the upper limit of the addition amount, it is preferably not more than 5.0% by weight with respect to the dispersion medium, more preferably not more than 4.0% by weight, and further preferably not more than 3.0% by weight. With the addition amount more than 5.0% by weight, the amount of hydroxyapatite sintered compact remaining in the dispersion liquid becomes significantly greater than the amount of that adhered to the surface of the polymer-based material. This is not preferable in the economic view.

As to the lower limit of the reaction temperature upon reacting the hydroxyl group of the hydroxyapatite sintered compact adhered to the surface of the polymer-based material and the functional group thereof to each other, it is preferably not less than 25° C., more preferably not less than 50° C., and further preferably not less than 80° C. The reaction temperature less than 25° C. may cause inadequate reaction of the hydroxyapatite sintered compact to the functional group. As to the upper limit of the reaction temperature, it is preferably not more than 200° C., more preferably not more than 175° C., and further preferably not more than 150° C. The reaction temperature more than 200° C. may cause degradation of the polymer-based material.

In the foregoing method, it is more preferable that the polymer-based material having been soaked by the dispersion liquid is washed by the same solvent as the dispersion medium before it is reacted to the hydroxyapatite sintered compact. This is because the polymer-based material having been soaked by a solvent contains lamination of the hydroxyapatite sintered compact on the surface, and if the reaction is carried out with the lamination of the hydroxyapatite sintered compact, physicality of the polymer-based material may be ruined.

Further, the reaction may be carried out under vacuum according to circumstances. Performing the reaction process of the hydroxyapatite sintered compact and the functional group under vacuum enables quick manufacturing of a hydroxyapatite complex. Note that, in the reaction process under vacuum, the pressure for the reaction is preferably in a range between 0.01 mmHg (1.33 kPa) to 10 mmHg (13.3 kPa). When the functional group is an alkoxysilyl group, methanol (ethanol) generated during the reaction of the hydroxyl group of the hydroxyapatite sintered compact to the alkoxysilyl group as the functional group may be removed by the pressure in the foregoing range. Further, when the functional group is a blocked isocyanate group (protected isocyanate group), a blocking agent (e.g., phenol, imidazole, oxime etc.) generated during the reaction of the hydroxyl group of the hydroxyapatite sintered compact to the isocyanate group as the functional group may be removed by the pressure in the foregoing range.

Note that, reaction condition and the type of solvent in the introduction process and the reaction process may be changed according to the type of the polymer-based material and the type of the functional group.

[Hydroxyapatite Complex]

The hydroxyapatite complex according to the present embodiment has such a structure that the hydroxyapatite sintered compact is chemically bonded on the surface of the polymer-based material. More specifically, a hydroxyl group (—OH) included in a hydroxyapatite sintered compact and an isocyanate group (—NCO) included in the polymer-based material or a linker modified the surface thereof are directly bonded in a chemical manner. When the alkoxysilyl group of the polymer-based material is —Si≡(OR)3, the bond between the hydroxyapatite sintered compact and the polymer-based material may be expressed by the following chemical formula (1).

(1)

where X expresses the polymer-based material, and Y expresses the hydroxyapatite sintered compact.

In this case, three hydroxyl groups of the hydroxyapatite sintered compact react with a —Si≡(OR)3 of the polymer-based material. Accordingly, a large amount of the hydroxyapatite sintered compact may be chemically bonded even to the polymer-based material containing less number of alkoxysilyl groups. On this account, in the case of introducing an alkoxysilyl group to the polymer-based material, the number of the alkoxysilyl groups may be reduced compared to a conventional method. Note that, the silicon atom (Si) of the formula (1) above is a part of the alkoxysilyl group contained in the polymer-based material. More specifically, the silicon atom may be a part of a graft chain with a modified surface or may be a part of the alkoxysilyl group contained in a polymeric chain. Further, the oxygen atom of the formula (1) above is a part of the alkoxysilyl group contained in the polymer-based material or a part of the hydroxyl group contained in the hydroxyapatite sintered compact. Further, X and Si of the formula (1) may be bonded through a polymeric chain, or may be bonded by a low molecular chain. Otherwise, the X and Si may be bonded directly.

Further, when the functional group is an isocyanate group, the hydroxyapatite sintered compact and the polymer-based material are chemically bonded through urethane bond.

Further, in the resulting hydroxyapatite complex, the thickness of the layer of the hydroxyapatite sintered compact is preferably, for example, in a range from 0.0001% to 100%, and further preferably in a range from 0.001% to 10% with respect to the entire thickness of the polymer-based material, in the usage as a percutaneous trans-catheter. These ranges however change depending on the thickness of the polymer-based material and/or the usage. By setting the thickness of the hydroxyapatite sintered compact layer to the foregoing ranges, it is possible to obtain a hydroxyapatite complex superior in biocompatibility without deteriorating the characteristic of the polymer-based material. Further, the resulting hydroxyapatite complex is also superior in flexibility due to the structure in which the hydroxyapatite sintered compact is chemically bonded on the surface of the polymer-based material.

As described, the hydroxyapatite complex according to the present embodiment has desirable flexibility and strength, and also superior in adherence and compatibility with respect to a living body. With these advantages, the hydroxyapatite complex may be used as a percutaneous medical implement, such as a percutaneous trans-catheter, a percutaneous terminal etc.; or as other medical materials, such as an artificial blood vessel, an artificial organ (e.g., a prosthesis) etc. Further, in contrast to the conventional method, the manufacturing method of the present embodiment enables easier manufacturing of a hydroxyapatite complex with more complicated structure.

Further, the hydroxyapatite complex of the present embodiment may be coated with a layer of a calcium phosphate compound according to the usage. The calcium phosphate compound to be laminated on the hydroxyapatite complex does not necessarily have to be the foregoing hydroxyapatite sintered compact.

The following describes possible methods of coating the hydroxyapatite complex with a layer of a calcium phosphate compound. For the first method, mixed particles made of polymeric monomers and calcium phosphate compounds are applied onto the hydroxyapatite complex, i.e., on that surface of the polymer-based material, which is modified by the hydroxyapatite sintered compact, and the polymeric monomers are then solidified through polymerization by heat, light, radiation etc. For the second method, the hydroxyapatite complex is soaked in a solution containing calcium ion and phosphate ion so as to extract the calcium phosphate compound. For the third method, the hydroxyapatite complex is soaked alternately in a solution containing calcium ion and a solution containing phosphate ion so as to extract the calcium phosphate compound. Further, in the first method above, the layer of the calcium phosphate compound may be formed in an arbitrary shape by using a mold.

Further, the manufacturing method of the present embodiment may be a method comprising the step of reacting the hydroxyapatite sintered compact with the polymer-based material, that contains at least one functional group selected from a group consisting of an isocyanate group and an alkoxysilyl group.

Further, the manufacturing method of the present embodiment may be a method in which a hydroxyapatite sintered compact and a polymer-based material containing an isocyanate group and/or an alkoxysilyl group are chemically bonded wherein the hydroxyl group of the hydroxyapatite sintered compact is chemically bonded directly to the isocyanate group and/or the alkoxysilyl group of the polymer-based material.

Further, the hydroxyapatite complex of the present embodiment is preferably made through the foregoing manufacturing method.

As described, the present invention provides a manufacturing method of a hydroxyapatite complex including a hydroxyapatite sintered compact and a polymer-based material that are chemically bonded, comprising the step of: a) reacting the hydroxyapatite sintered compact with a functional group of the polymer-based material, that contains at least one functional group selected from a group consisting of an isocyanate group and an alkoxysilyl group.

With this structure, the hydroxyapatite sintered compact is reacted with the functional group of the polymer-based material. The isocyanate group and/or the alkoxysilyl group is chemically bonded directly with a hydroxyl group (—OH) contained in the hydroxyapatite sintered compact.

On this account, in contrast to the conventional method, it is not necessary to introduce an active group in the hydroxyapatite sintered compact in order to react the functional group with the active group. Namely, it is not necessary to perform a chemical pre-treatment with respect to the hydroxyapatite sintered compact, thus performing manufacturing of the hydroxyapatite sintered compact in an easier way than the conventional way.

Further, since this method allows omission of the chemical pre-treatment, there are no risks of degradation or changes in bioactivity of the hydroxyapatite sintered compact.

Further, as described, the present invention provides a manufacturing method of a hydroxyapatite complex including a hydroxyapatite sintered compact and a polymer-based material that are chemically bonded, comprising the steps of: a) introducing at least one functional group selected from a group consisting of an isocyanate group and an alkoxysilyl group into the polymer-based material; and b) reacting the hydroxyapatite sintered compact with the functional group of the polymer-based material.

The foregoing structure uses a polymer-based material in which at least one functional group selected from a group consisting of an isocyanate group and an alkoxysilyl group is introduced. This structure allows the use of various polymer-based materials.

With the foregoing structure, the hydroxyapatite sintered compact is chemically bonded directly with the isocyanate group and/or the alkoxysilyl group. Therefore, in contrast to the conventional method, it is not necessary to introduce a reactive functional group in the hydroxyapatite sintered compact in order to react the functional group with the reactive functional group. Namely, it is not necessary to perform a chemical pre-treatment with respect to the hydroxyapatite sintered compact, thus performing manufacturing of the hydroxyapatite sintered compact in an easier way.

Further, the manufacturing method of the hydroxyapatite complex according to the present invention may be arranged so that the step (a) is performed using a compound, that contains a reactive functional group and at least one functional group selected from a group consisting of an isocyanate group and an alkoxysilyl group, so as to react the reactive functional group with the polymer-based material.

This method performs introduction of the isocyanate group and/or the alkoxysilyl group in the polymer-based material by reacting the reactive functional group of the compound and the polymer based material. With this method, introduction of the functional group may be performed with less number of processes.

Further, the manufacturing method of the hydroxyapatite complex according to the present invention preferably further includes the step of: c) introducing an active group into the polymer-based material before the step (a), wherein the step (a) is performed using a compound, that contains a reactive functional group and at least one functional group selected from a group consisting of an isocyanate group and an alkoxysilyl group, so as to react the reactive functional group with the active group of the polymer-based material.

The foregoing method performs introduction of an active group in the polymer-based material so that the reactive functional group is reacted with the active group. This structure allows the use of various functional groups. On this account, the introduction of the functional group may be performed in an easier way.

Further, the manufacturing method of the hydroxyapatite complex according to the present invention is preferably arranged so that the compound is a silane coupling agent.

The silane coupling agent includes an alkoxysilyl group and a reactive functional group. With this agent, the alkoxysilyl group may be easily introduced in the polymer-based material.

Further, the manufacturing method of the hydroxyapatite complex according to the present invention is preferably arranged so that the polymer-based material is a medical polymeric material.

Further, it is preferable that the medical polymeric material is silk fibroin.

With this method using a medical polymeric material as the polymer-based material, it is possible to manufacture a hydroxyapatite complex having high biocompatibility.

As described, the present invention provides a hydroxyapatite complex in which a hydroxyapatite sintered compact and a polymer-based material containing an isocyanate group and/or an alkoxysilyl group are chemically bonded, wherein the hydroxyapatite sintered compact is chemically bonded directly to the isocyanate group and/or the alkoxysilyl group of the polymer-based material.

With the foregoing method in which the hydroxyapatite sintered compact is chemically bonded directly to the isocyanate group and/or the alkoxysilyl group of the polymer-based material, it is not necessary to perform a chemical pre-treatment with respect to the hydroxyapatite sintered compact, in contrast to the conventional method.

Further, in the foregoing method, the hydroxyapatite sintered compact is chemically bonded directly to the functional group (the isocyanate group and/or the alkoxysilyl group) of the polymer-based material. Therefore, the structure is immune to the problem of residue of the active group on the surface of the calcium phosphate in contrast to the conventional method in which an active group is introduced in calcium phosphate. Thus, in contrast to the conventional structure, this structure is immune to a risk of degradation in bioactivity of the calcium phosphate due to the residue of the active group.

Further, as described, the present invention provides a hydroxyapatite complex in which a hydroxyapatite sintered compact and a polymer-based material containing an alkoxysilyl group are chemically bonded, wherein: the hydroxyapatite sintered compact is chemically bonded to the polymer-based material with a molecular chain expressed as:

(1)

where X expresses the polymer-based material, and Y expresses the hydroxyapatite sintered compact.

Further, as described, the medical material according to the present invention uses the foregoing hydroxyapatite complex.

With the use of the foregoing hydroxyapatite complex, it is possible to provide a medical material with high bioactivity and improved reliability.

Further, as described, the present invention provides a manufacturing method of a hydroxyapatite complex including a hydroxyapatite sintered compact and a polymer-based material, comprising the step of: a) reacting the hydroxyapatite sintered compact with a functional group of the polymer-based material, that contains at least one functional group selected from a group consisting of an isocyanate group and an alkoxysilyl group, so as to chemically bond the hydroxyapatite sintered compact and the polymer-based material.

Further, as described, the present invention provides a manufacturing method of a hydroxyapatite complex including a hydroxyapatite sintered compact and a polymer-based material, comprising the steps of: a) introducing at least one functional group selected from a group consisting of an isocyanate group and an alkoxysilyl group into the polymer-based material; and b) reacting the hydroxyapatite sintered compact with the functional group of the polymer-based material so as to chemically bond the hydroxyapatite sintered compact with the polymer-based material.

EXAMPLES

The present invention is more specifically explained below with some concrete examples and corresponding comparative examples. It should be noted that the present invention is not restricted by those examples.

Example 1

[Manufacturing Method of Hydroxyapatite Sintered Compact]

The following will explain a manufacturing method of a hydroxyapatite sintered compact according to the present invention.

Firstly, a 40 ml continuous oil phase containing a 0.5 g nonionic surfactant is prepared by using dodecane as a continuous oil phase and penta ethylene glycol dodecyl ether as a nonionic surfactant whose clouding point is 31° C. Then, 10 ml of Ca (OH)2 dispersed aqueous solution (2.5 mole %) was added to the resulting continuous oil phase. The resulting dispersion solution was sufficiently stirred to be a water/oil (W/O) emulsion, which was then mixed with a 10 ml of 1.5 mole % KH2PO4 solution. The emulsion and the KH2PO4 solution were reacted by being stirred for 24 hours at 50° C. The product was then subjected to centrifugal separation so as to obtain hydroxyapatite. The hydroxyapatite was heated for an hour at 800° C. so as to obtain hydroxyapatite sintered compact particles. Each particle has a single-crystal structure with a major axis ranging from 100 nm to 250 nm.

[Manufacturing Method of Hydroxyapatite Complex]

A fibriform of silk fibroin (Habutae produced by Fujimura silk-reeling Corporation: hereinafter referred to as a SF fiber) of 275.24 mg that had been through vacuum drying for a whole day and night, used as a polymer-based material, 34 ml of anhydrous dimethylsulfoxide, 6.0 mg of hydroquinone as a polymerization inhibitor, 27 µl of dibutyltin (IV) dilaurate as a catalyst, and 550 mg of 2-methacryloyloxyethylisocyanate (hereinafter referred to as MOI) were mixed in a three-necked flask of 200 ml in capacity. These materials were reacted to each other for 6 hours at 50° C. so as to obtain a silk fibroin fiber in which a vinyl group is introduced. The introduction ratio of MOI was 23.3% by weight.

Next, the 51.99 mg of silk fibroin fiber having a vinyl group (hereinafter referred to as a vinyl introduction SF), 10 ml of anhydrous toluene, 132.19 mg of azobisisobutyronitrile as an initiator, and 1.0 g of methacryloxypropylmethyldimethoxysilane (Product No KBM-503 produced by Shin-Etsu Chemical Co.Ltd: hereinafter referred to as KBM) were contained in a polymer glass tube, and then were subjected to several sets of deairing/nitrogen gas filling. Then, the materials were sealed to react with each other at 60° C. for a predetermined period. The resultant is a silk fibroin fiber (hereinafter referred to as KBM-g-SF) in which a high molecular chain containing an alkoxysilyl group in its end is bonded to a polymer-based material through graft polymerization. Table 1 shows the introduction ratio (%) of alkoxysilyl group in this case at each given reaction time. Note that, the introduction ratio was found according to the following Formula (1), in which ag expresses the weight of the vinyl introduced SF and bg expresses the weight of the KBM-g-SF.

$$\text{Introduction ratio (\%)} = ((b-a)/a) \times 100 \qquad (1)$$

TABLE 1

| | REACTION TIME (h) | | | | |
|---|---|---|---|---|---|
| | 0.3 | 0.5 | 1.0 | 2.0 | 4.0 |
| INTRODUCTION RATIO(% BY WEIGHT) | 17.0 | 20.8 | 27.4 | 28.3 | 29.4 |

Figure 1:
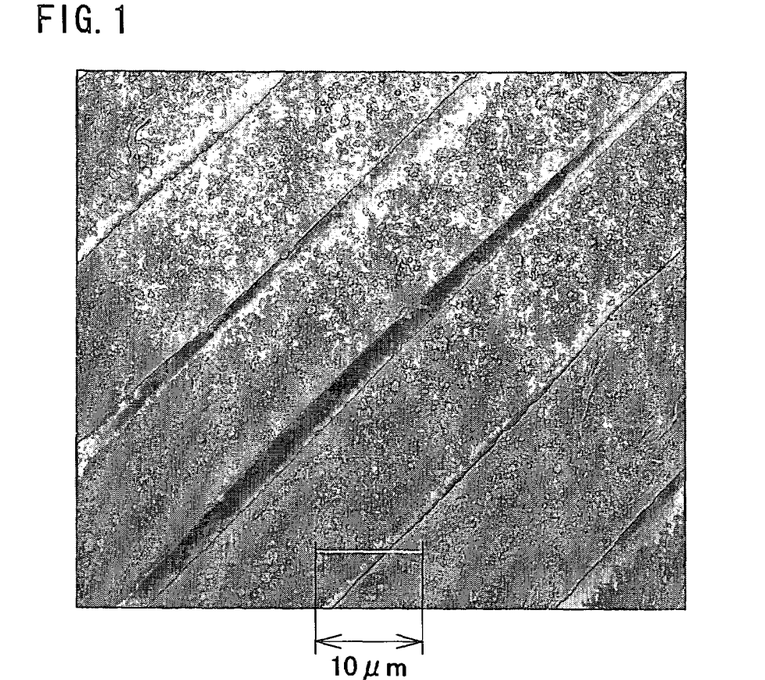
FIG. 1 is a drawing illustrating an image of a surface of a hydroxyapatite complex according to Example 1.

Then, the hydroxyapatite sintered compact particles created in the manner above was dispersed in an amount of 10 mg per ml in a mixture solvent that contains toluene and methanol with a volume ratio of 9:1. Then, the KBM-g-SF is cut into a disc shape (with a diameter of 1.5 cm) and is dipped in the mixture solvent. After taken out of the solvent, the KBM-g-SF is fully washed by toluene, before subjected to coupling reaction for 2 hours at 120° C. under vacuum. After the reaction, the product is soaked in distilled water before processed for 3 minutes with a probe-type supersonic generating device (Type W-220F produced by WAKENYAKU Co. Ltd) under the condition of 20 kHz and 35 W, so as to remove unreacted hydroxyapatite sintered compact particles. As a result, the hydroxyapatite complex of the present invention is obtained. The hydroxyapatite complex was observed with a scanning electron microscope. FIG. 1 shows the result of observation.

With this result of observation, it was found that the hydroxyapatite sintered compact particles are bonded to the surface of the SF fiber.

Comparative Example 1

Figure 2:
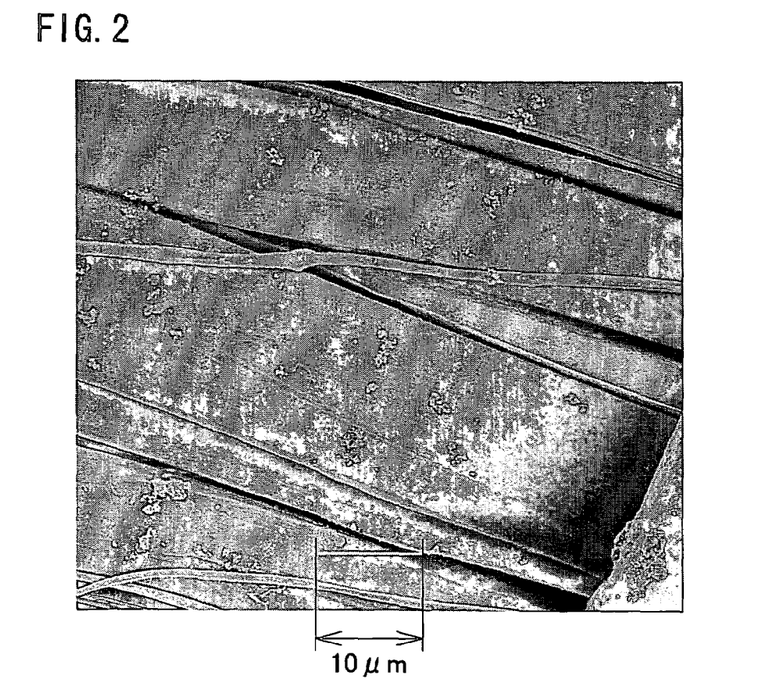
FIG. 2 is a drawing illustrating an image of a surface of a hydroxyapatite complex according to Comparative example 1.

The same SF fiber as above however not having an alkoxysilyl group is soaked into the hydroxyapatite sintered compact particles dispersed solvent so that the hydroxyapatite sintered compact particles are adhered to the SF fiber. The product is then soaked in distilled water before processed for 3 minutes by a probe-type supersonic generating device (the same device as above) under the condition of 20 kHz and 35 W so as to remove unreacted hydroxyapatite sintered compact particles. The resulting hydroxyapatite complex was observed with a scanning electron microscope. FIG. 2 shows the result of observation.

With this result of observation, it was found that the hydroxyapatite sintered compact particles are not bonded to the surface of the SF fiber.

Example 2

A 50 mg of SF fiber that had as a polymer-based material, 6 ml of distilled water, 41 mg of persulfuric ammonium of 41 mg as an initiator, 73 mg of penta ethylene glycol dodecyl ether as a nonionic surfactant, 435 mg of 2-(o-[1'-methyl propylidene amino] carboxylamino) ethylmethacryate (Lot No. 30K01 produced by SHOWA DENKO K. K: hereinafter referred to as MOI-BM) were mixed in a test tube. The mixed materials were then subjected to sets of deairing/nitrogen gas filling sufficient times. Then, the materials were sealed to react with each other at 50° C. for a predetermined period. The resultant is a silk fibroin fiber (hereinafter referred to as MOI-BM-g-SF) in which a high molecular chain containing an isocyanate group blocked by oxime (hereinafter referred to as a blocked isocyanate group) in its end is bonded to a polymer-based material through graft polymerization. Table 2 shows the introduction ratio (%) of the blocked isocyanate group in this case at each given reaction time. Note that, the introduction ratio was found according to the following Formula (2), in which cg expresses the weight of unprocessed SF fiber and dg expresses the weight of the MOI-BM-g-SF.

$$\text{Introduction ratio (\%)} = ((d-c)/c) \times 100 \qquad (2)$$

TABLE 2

| | REACTION TIME (h) | |
|---|---|---|
| | 1.0 | 2.0 |
| INTRODUCTION RATIO(% BY WEIGHT) | 4.5 | 10.3 |

Figure 3:
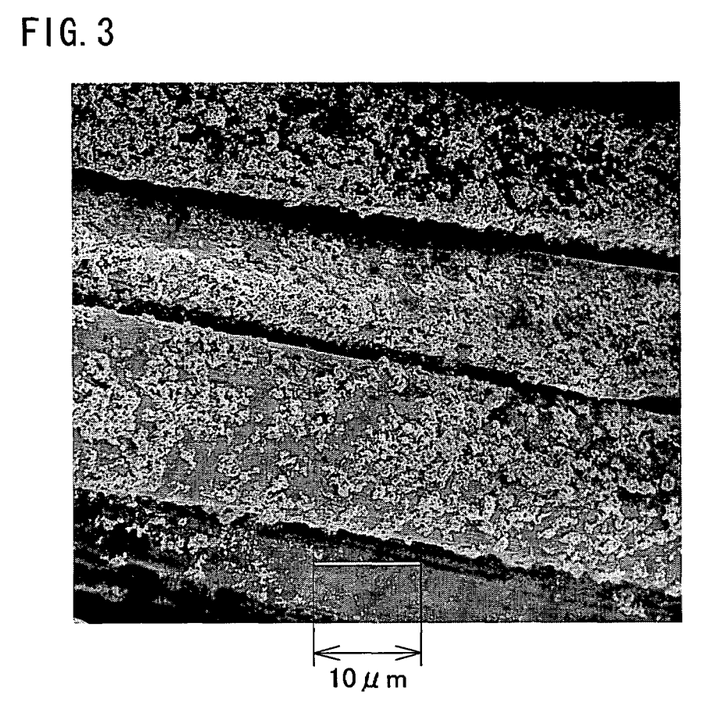
FIG. 3 is a drawing illustrating an image of a surface of a hydroxyapatite complex according to Example 2.

Then, the hydroxyapatite sintered compact particles created in the same manner as Example 1 was dispersed in an amount of 10 mg per ml in a mixture solvent that contains toluene and methanol with a volume ratio of 9:1. Then, a disc-shaped MOI-BM-g-SF with a diameter of 1.5 cm is soaked in the dispersion solvent. After taken out of the solvent, the KBM-g-SF is fully washed by the mixture solvent, before subjected to coupling reaction for 20 minutes at 140° C. under vacuum. After the reaction, the product is soaked in distilled water before processed for 3 minutes by a probe-type supersonic generating device (the same device as above) under the condition of 20 kHz and 35 W, so as to remove unreacted hydroxyapatite sintered compact. As a result, the hydroxyapatite complex of the present invention is obtained. The hydroxyapatite complex was observed with a scanning electron microscope. FIG. 3 shows the result of observation.

With this result of observation, it was found that the hydroxyapatite sintered compact particles are bonded to the surface of the SF fiber.

Comparative Example 2

The same SF fiber as above however not having the isocyanate group is soaked into the hydroxyapatite sintered compact particles dispersed solvent so that the hydroxyapatite sintered compact particles are adhered to the SF fiber. The product is then soaked in distilled water before processed for 3 minutes by a probe-type supersonic generating device (the same device as above) under the condition of 20 kHz and 35

Figure 4:
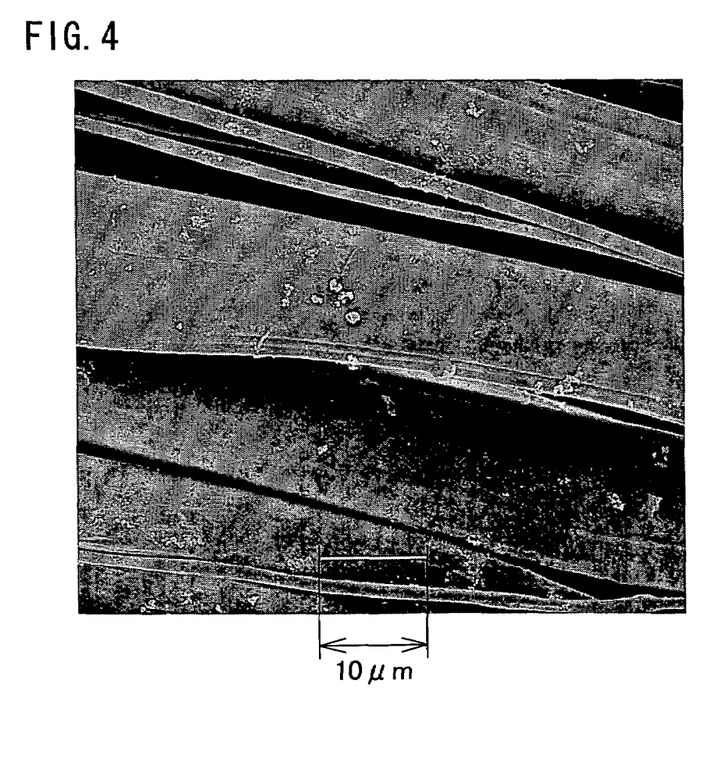
FIG. 4 is a drawing illustrating an image of a surface of a hydroxyapatite complex according to Comparative example 2.

W so as to remove unreacted hydroxyapatite sintered compact. The resulting hydroxyapatite complex was observed with a scanning electron microscope. FIG. 4 shows the result of observation.

With this result of observation, it was found that the hydroxyapatite sintered particles are not bonded to the surface of the SF fiber.

Example 3

First prepared was a reagent created by mixing 73 mg of penta ethylene glycol dodecyl ether as a nonionic surfactant, and 323 mg of the KBM. The reagent was then added to a test tube containing a 50 mg of SF fiber, 6 ml of distilled water, and persulfuric ammonium of 41 mg. The mixed materials were stirred, and then subjected to sets of deairing/nitrogen gas filling sufficient times. Then, the materials were sealed to react with each other at 50° C. for a predetermined period. The resultant is a SF fiber (hereinafter referred to as KBM-SF) which is bonded to a high molecular chain containing an alkoxysilyl group in its end through graft polymerization. Table 3 shows the introduction ratio (%) of the alkoxysilyl group in this case at each given reaction time. Note that, the introduction ratio was found according to the following Formula (3), in which eg expresses the weight of unprocessed SF fiber and fg expresses the weight of the KBM-SF.

$$\text{Introduction ratio (\%)} = ((f-e)/e) \times 100 \quad (3)$$

TABLE 3

| | REACTION TIME (min) | | | | |
|---|---|---|---|---|---|
| | 10 | 20 | 30 | 40 | 50 |
| INTRODUCTION RATIO (% BY WEIGHT) | 8.7 | 13.8 | 16.6 | 15.2 | 16.3 |

Figure 5:
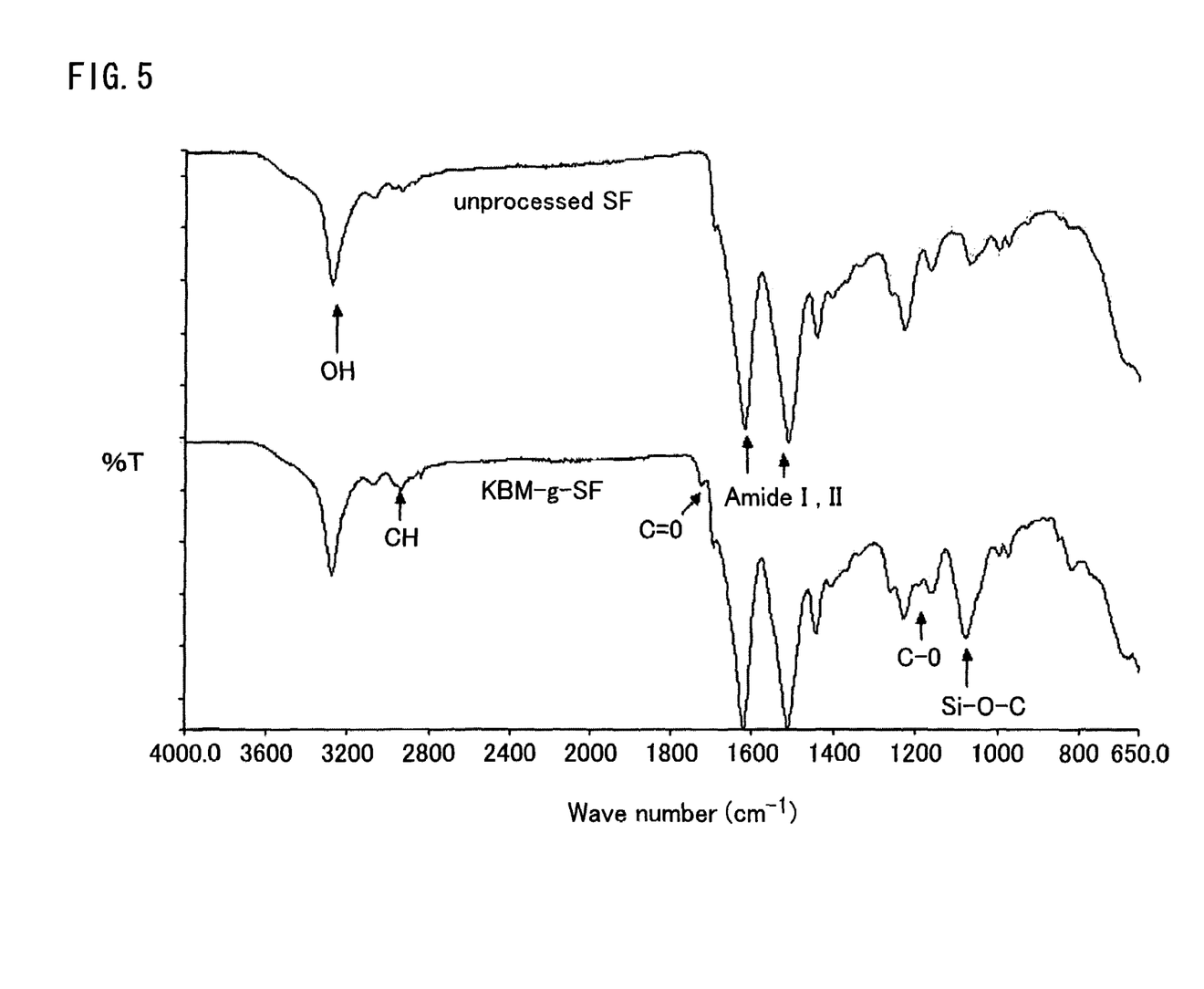
FIG. 5 is a spectrum showing a result of FT-IR analysis of KBM-SF of Example 3.

FIG. 5 shows FT-IR analysis result of the KBM-SF obtained in the method above. Note that, the unprocessed SF is a spectrum denoting a result of FT-IR analysis of the polymer-based material, and the lower spectrum denotes FT-IR analysis of the KBM-SF.

Figure 6:
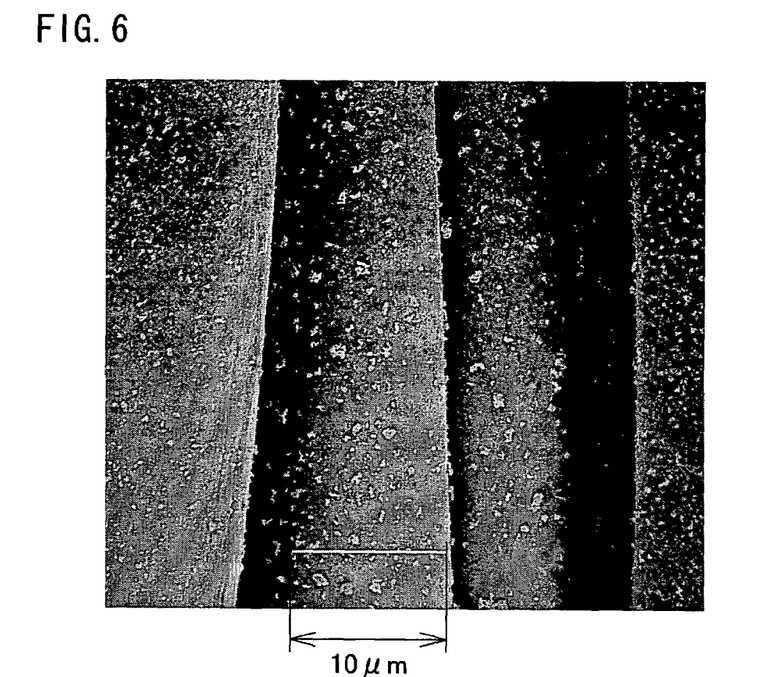
FIG. 6 is a drawing illustrating an image of a surface of a hydroxyapatite complex according to Example 3.

Then, the hydroxyapatite sintered compact particles created in the same manner as Example 1 was dispersed in an amount of 5 mg per ml in a mixture solvent that contains toluene and methanol with a volume ratio of 8.8:1, and then was left still for an hour. Then, a disc-shaped KBM-SF with a diameter of 1.8 cm is soaked in the mixture solvent. After taken out of the solvent, the KBM-SF is fully washed by the mixture solvent, before subjected to coupling reaction for 2 hours at 120° C. After the reaction, the product is soaked in distilled water before processed for 3 minutes by a probe-type supersonic generating device (the same device as above) under the condition of 20 kHz and 35 W so as to remove unreacted hydroxyapatite sintered compact particles. As a result, the hydroxyapatite complex of the present invention is obtained. The hydroxyapatite complex was observed with a scanning electron microscope. FIG. 6 shows the result of observation.

With this result of observation, it was found that the hydroxyapatite sintered particles are bonded to the surface of the SF fiber.

[Cell Adhesion Test]

The following describes a cell adhesion test of the hydroxyapatite complex obtained by the method of Example 3.

The hydroxyapatite complex and the unprocessed fiber (SF fiber) are placed still in a 24 multi well dish. Then, 1×105 of mouse fibroblast (L929) is inoculated to each of the complex and the fiber, respectively. Note that, the unprocessed fiber only refers to the polymer-based material, and therefore corresponds to a comparative example. Then, the resultants are cultivated with a culture solution of α-MEM LB medium (containing 10% of bovine serum, 50IU penicillin, 50 μg/ml of streptomycin, 2.550 μg/ml of amphotericin B) for a whole day and night.

Figure 7:
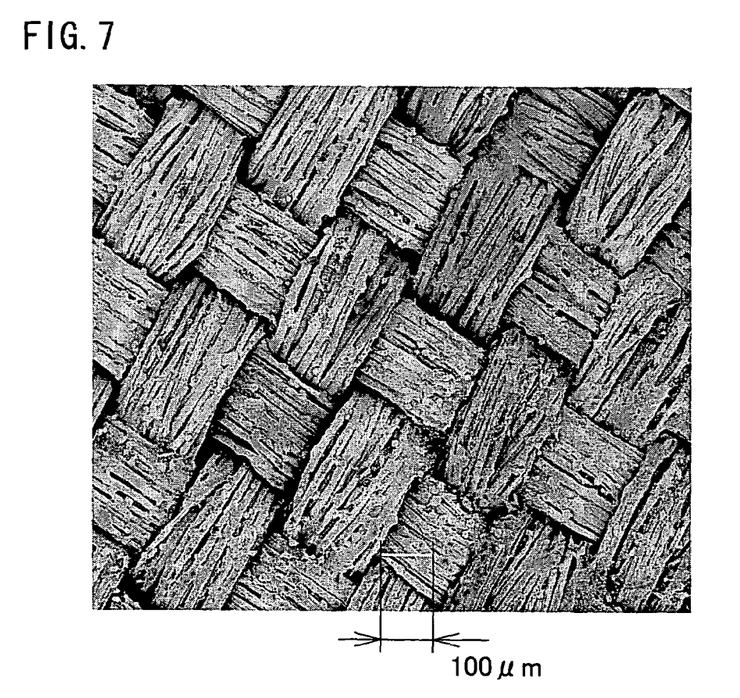
FIG. 7 is a drawing illustrating an image in a scanning electron microscope, showing a result of a cell adherence test using a hydroxyapatite complex of Example 3.
Figure 8:
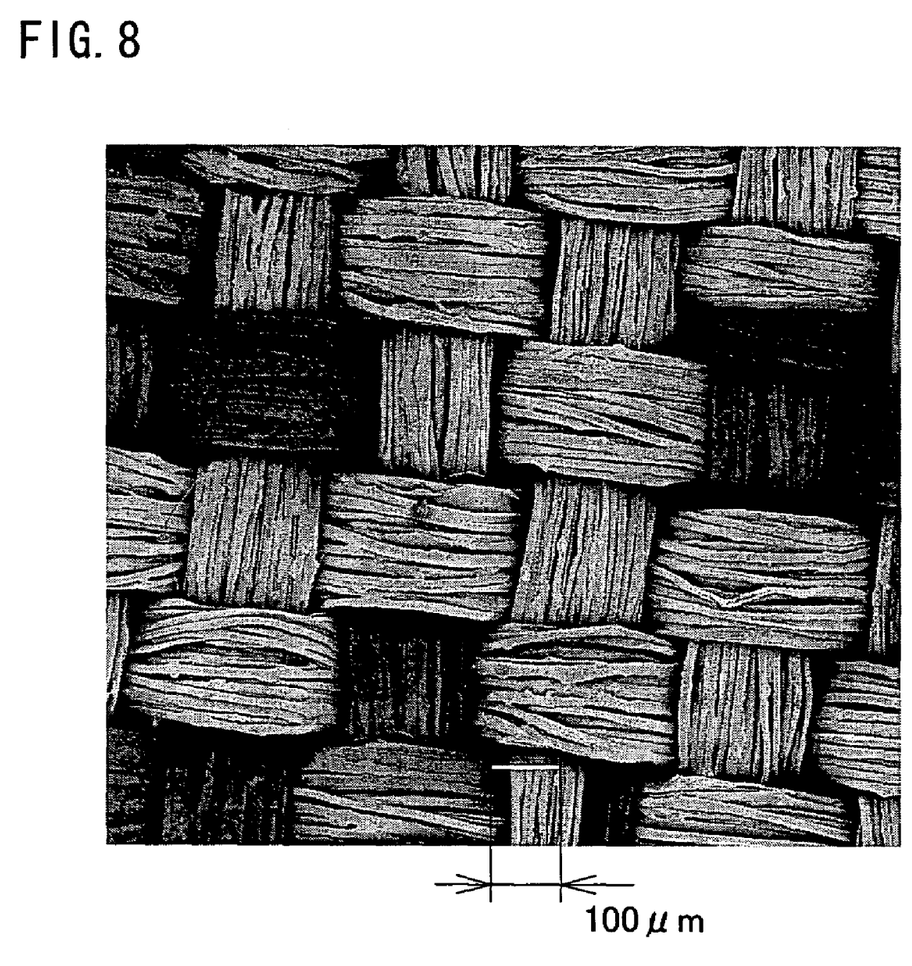
FIG. 8 is a drawing illustrating an image in a scanning electron microscope, showing a result of a cell adherence test using only a polymer-based material for a comparative example.

After the cultivation, the hydroxyapatite complex and the unprocessed fiber are sufficiently washed by a phosphate buffer, and then observed with a scanning electron microscope after the fibroblasts are fixed. The observation results are shown in FIG. 7 for the hydroxyapatite complex, and in FIG. 8 for the unprocessed fiber. These figures reveal that the hydroxyapatite complex shows significant improvement of cell adherence, compared to the unprocessed fiber.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The invention is useful for a percutaneous medical implement, such as a percutaneous trans-catheter, a percutaneous terminal etc.; or for other medical materials, such as an artificial blood vessel, an artificial organ (e.g., a prosthesis) etc.

The invention claimed is:

1. A manufacturing method of a hydroxyapatite complex including a hydroxyapatite sintered compact and a polymer-based material, comprising the step of:
    a) reacting the hydroxyapatite sintered compact with an alkoxysilyl group of the polymer-based material, so as to chemically bond the hydroxyapatite sintered compact and the polymer-based material.

2. The manufacturing method of a hydroxyapatite complex as set forth in claim 1, wherein:
    the polymer-based material is a medical polymeric material.

3. The manufacturing method of a hydroxyapatite complex as set forth in claim 2, wherein:
    the medical polymeric material is a silk fibroin.

4. A manufacturing method of a hydroxyapatite complex including a hydroxyapatite sintered compact and a polymer-based material, comprising the steps of: a) introducing an alkoxysilyl group into the polymer-based material; and b) reacting the hydroxyapatite sintered compact with the alkoxysilyl group of the polymer-based material so as to chemically bond the hydroxyapatite sintered compact with the polymer-based material.

5. The manufacturing method of a hydroxyapatite complex as set forth in claim 4, wherein: the step (a) is performed using a compound, that contains a reactive functional group and an alkoxysilyl group, so as to react the reactive functional group with the polymer-based material.

6. The manufacturing method of a hydroxyapatite complex as set forth in claim 5, wherein:
    the compound is a silane coupling agent.

7. The manufacturing method of a hydroxyapatite complex as set forth in claim 4, further comprising the step of:
    c) introducing an active group into the polymer-based material before the step (a),
    wherein:

the step (a) is performed using a compound, that contains a reactive functional group and at least one functional group and an alkoxysilyl group, so as to react the reactive functional group with the active group of the polymer-based material.

8. The manufacturing method of a hydroxyapatite complex as set forth in claim 7, wherein:
the compound is a silane coupling agent.

9. A manufacturing method of a hydroxyapatite complex comprising a hydroxyapatite sintered compact and a polymer-based material, comprising the step of:
reacting the hydroxyapatite sintered compact with an isocyanate group of silk fibroin, so as to form a chemical bond.

* * * * *

UNITED STATES PATENT AND TRADEMARK OFFICE
CERTIFICATE OF CORRECTION

PATENT NO. : 7,473,731 B2  Page 1 of 1
APPLICATION NO. : 10/506429
DATED : January 6, 2009
INVENTOR(S) : Furuzono et al.

It is certified that error appears in the above-identified patent and that said Letters Patent is hereby corrected as shown below:

On the Title pg, should read
Item (54) HYDROXYAPATITE COMPLEX AND MANUFACTURING METHOD THEREOF, MEDICAL MATERIAL USING HYDROXYAPATITE COMPLEX Signed and Sealed this Twenty-first Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,473,731 B2
APPLICATION NO. : 10/506429
DATED : January 6, 2009
INVENTOR(S) : Furuzono et al.

Page 1 of 1

It is certified that error appears in the above-identified patent and that said Letters Patent is hereby corrected as shown below:

On the Title pg Item (54) and Column 1, lines 1-4, should read
HYDROXYAPATITE COMPLEX AND MANUFACTURING METHOD THEREOF, MEDICAL MATERIAL USING HYDROXYAPATITE COMPLEX This certificate supersedes the Certificate of Correction issued April 21, 2009.

Signed and Sealed this

Twelfth Day of May, 2009

JOHN DOLL
*Acting Director of the United States Patent and Trademark Office*